United States Patent
Bhalla (12) United States Patent (10) Patent No.: US 7,357,778 B2
(45) Date of Patent: Apr. 15, 2008

(54) AQUEOUS DRAINAGE AND FLOW REGULATING IMPLANT

(76) Inventor: Ajay Bhalla, 2236 Mandrill Ave., Ventura, CA (US) 93003

( * ) Notice: Subject to any disclaimer, the term of this patent is extended or adjusted under 35 U.S.C. 154(b) by 338 days.

(21) Appl. No.: 11/130,076

(22) Filed: May 17, 2005

(65) Prior Publication Data

US 2005/0267397 A1    Dec. 1, 2005

Related U.S. Application Data

(60) Provisional application No. 60/572,422, filed on May 20, 2004.

(51) Int. Cl.
*A61M 5/00* (2006.01)
(52) U.S. Cl. .............. 604/9; 604/8; 604/264; 606/153
(58) Field of Classification Search .............. 604/7–10, 604/6.1, 264; 606/153
See application file for complete search history.

(56) References Cited

U.S. PATENT DOCUMENTS

| | | | |
|---|---|---|---|
| 4,457,757 A | 7/1984 | Molteno | |
| 4,554,918 A | 11/1985 | White | |
| 4,729,761 A * | 3/1988 | White | ............ 604/8 |
| 5,397,300 A | 3/1995 | Baerveldt | |
| 5,411,473 A | 5/1995 | Ahmed | |
| 5,454,796 A | 10/1995 | Krupin | |
| 5,476,445 A | 12/1995 | Baerveldt | |
| 5,616,118 A | 4/1997 | Ahmed | |
| 5,752,928 A * | 5/1998 | de Roulhac et al. | ............ 604/8 |
| 7,025,740 B2 * | 4/2006 | Ahmed | ............ 604/9 |

* cited by examiner

*Primary Examiner*—Leslie R. Deak (57) ABSTRACT

For use in controlling the release of aqueous from anterior chamber of the eye, a surgically implantable flow regulating implant is provided which is assembled in parts from a molded elastomeric plate, a flow regulating member and drainage tube. The elastomeric plate contains a pocket, a circular passageway and slots. The flow regulating member includes tabs and a resilient membrane, said tabs are securely attached to the plate inside the slots to support the membrane. The membrane being generally arch-shaped completely covers the pocket forming a releasable seal between the said pocket and outer surface of the said plate.

11 Claims, 7 Drawing Sheets

AQUEOUS DRAINAGE AND FLOW REGULATING IMPLANT

I request to claim priority of provisional application No. 60/572,422, filed May 20, 2004.

BACKGROUND OF INVENTION

Glaucoma is a group of diseases that can damage the eye's optic nerve and result in vision loss and blindness. Glaucoma is a common problem in aging, where the pressure within the eye becomes elevated. There are three chambers of fluid in the eye: Anterior chamber (between cornea and iris), Posterior chamber (between iris, zonule fibers and lens) and the Vitreous chamber (between the lens and the retina). The first two chambers are filled with aqueous humor whereas the vitreous chamber is filled with a more viscous fluid, the vitreous humor. Normally aqueous humor secreted by the ciliary body courses through the posterior chamber, around the iris into the anterior chamber, and exits out through a spongy tissue at the front of the eye called the trabecular meshwork into Schlemen's canal, aqueous and episcleral veins. The delicate balance between the production and drainage of aqueous determines the eye's intraocular pressure (IOP). In patients with glaucoma, the outflow of aqueous fluid becomes restricted, thereby increasing the intraocular pressure, which in turn presses on the optic disk, and eventually compressing the incoming retinal blood vessels and the axons of the ganglion cells so that these vital cells die. Treatment to reduce the intraocular pressure is essential in glaucoma Prescribing eye drops is usually the first step in lowering the IOP. Most medications reduce the eye pressure by decreasing the production of aqueous. However, because the aqueous supplies nourishment to the front of the eye, the body has a built-in mechanism that limits the extent the eye's pressure can be lowered with medication. Other medications work by improving the outflow of fluid from the eye. Medication treatment is expensive and often have side effects associated with it. Furthermore, these expensive drugs are not readily available in rural and undeveloped regions.

When medications no longer controls the eye pressure adequately, surgery may be needed. Trabeculectomy is one type of glaucoma surgery that is commonly performed. It involves making a tiny filtering valve in the sclera (the white of the eye). The aqueous drains out of the front of the eye through the tiny opening where it collects underneath the clear conjunctival tissue that covers the sclera. One of the most common problems with trabeculectomy is that it lowers the pressure too well, which can cause complications and significantly lengthen the recovery time. Another disadvantage of this procedure is that the body's natural healing process may gradually close the filter, causing the pressure to become elevated again. Another surgical procedure performed is iridectomy when iris root blocks the entrance to the trabecular meshwork thereby impeding the flow of aqueous humor. A hole in the iris (Iridectomy) can be surgically created to relieve the blockage. The disadvantage associated with this procedure is that the tissue of the eye may gradually close the opening created, thereby requiring the need for further treatment.

Drainage implant is another widely used corrective method for glaucoma treatment. One such device is discussed by Anthoney C. B. Molteno in U.S. Pat. No. 4,457,757. This device comprises of a rigid plate having a tube that extends into the intraoccular chamber. The aqueous humor from the intraoccular chamber flows onto the surface of the plate and is absorbed by the body. This implant is not desirable since plates are formed of rigid plastic material, which may cause post operative irritation and difficulty during insertion in the eye. Furthermore, the Molteno plate does not have any pressure controlling mechanism, and thus always has associated risk of causing hypotony.

U.S. Pat. No. 4,554,918, issued to Thomas C. White suggests one type of glaucoma valve where the aqueous humor flows from the intraoccular chamber through a tube into an external reservoir. The end of the tube in contact with the reservoir has unidirectional valve, which is basically a small opening. The small opening provides limited resistance to flow of the aqueous humor. When the reservoir gets filled, patient is supposed to press the reservoir so as to force aqueous humor out into the body for absorption. This feature makes this device undesirable for long term glaucoma treatment. Furthermore, the small opening can get clogged by biological particulates present in the viscous aqueous humor, posing potential risk of valve dysfuntionoing.

In a glaucoma shunt disclosed by Ahmed in U.S. Pat. No. 5,411,473, a valve is added to the basic Molteno design. The valve claims to provide some protection against excessive aqueous outflow during the first few days after surgery. The valve includes a thin Silicone elastomeric sheet sandwiched between two rigid plates and a tube is attached to the silicone sheet. One of the drawbacks in the design is that, the tube end in communication with silicone sheet, gets compressed when sheet is sandwiched, thereby closing the aqueous outlet. This feature can cause valve clogging from prolonged use. Furthermore, the plates are formed of a rigid plastic material, which makes insertion beneath the eye tissue difficult and time consuming. The rigid plastic material poses a risk of irritation and/or damage to adjacent vasculature and tissue. Other non-valved implant described in Baerveldt, U.S. Pat. No. 5,476,445, is basically a device for releasing Intraoccular pressure. Since, no pressure regulating mechanism is available, it could lead to hypotony. Furthermore, the implant employs temporary sutures, which need to be removed after period of time, which in turn requires another surgery.

REFERENCES CITED

U.S. Patent Documents

| | | | |
|---|---|---|---|
| 4457757 | July 1984 | Molteno | 604/9 |
| 4554918 | November 1985 | White | 604/10 |
| 5397300 | March 1995 | Baerveldt | 604/8 |
| 5411473 | May 1995 | Ahmed | 604/8; 604/9 |
| 5476445 | December 1995 | Baerveldt | 604/8; 604/9 |
| 5454796 | October 1995 | Krupin | 604/9 |
| 5616118 | April 1997 | Ahmed | 604/8; 604/9 |

SUMMARY OF THE INVENTION

These problems in prior arts are overcome in large part by the present invention. The key features of this invention make this implant the most optimal design for regulated drainage of aqueous humor from the anterior chamber of the eye to relieve excess pressure without causing hypotony. The implant comprising of plate, flow regulating member and drainage tube, all are constructed from flexible elastomeric material, which implant provides trouble-free insertion beneath the eye and also reduces post-operative irritation whereas a known prior art with valve mechanism is made of relatively hard polypropylene material. Moreover, the apparatus of the present invention is relatively inexpensive to manufacture, and can be modified to provide a variety of pressure/flow characteristics.

The implant is sized and shaped to fit in between two adjacent rectus muscles. The implant is sutured to the eye and covered by a smooth layer of the patient's tissue, as well as donor tissue, such as sclera, which covers the extraocular portion of the tube. Once implanted, the scar tissue is formed around the plate thereby forming a drainage bleb. The implant has a small inlet tube that is surgically inserted in the anterior chamber of the eye allowing aqueous humor to flow from the anterior chamber to the plate pocket which is covered by resilient membrane, which membrane is integral part of flow regulating member. The resilient membrane is normally biased to prevent flow through the pocket, but will open to permit flow through the pocket when the pressure inside anterior chamber of the eye exceeds predetermined amount.

A variety of pressure/flow characteristics can be provided by the present invention by providing a resilient membrane in different thickness.

Other features and advantages of the present invention will become apparent from the following more detailed description, taken in conjunction with the accompanying drawings.

DETAILED DESCRIPTION OF THE INVENTION

Figure 1:
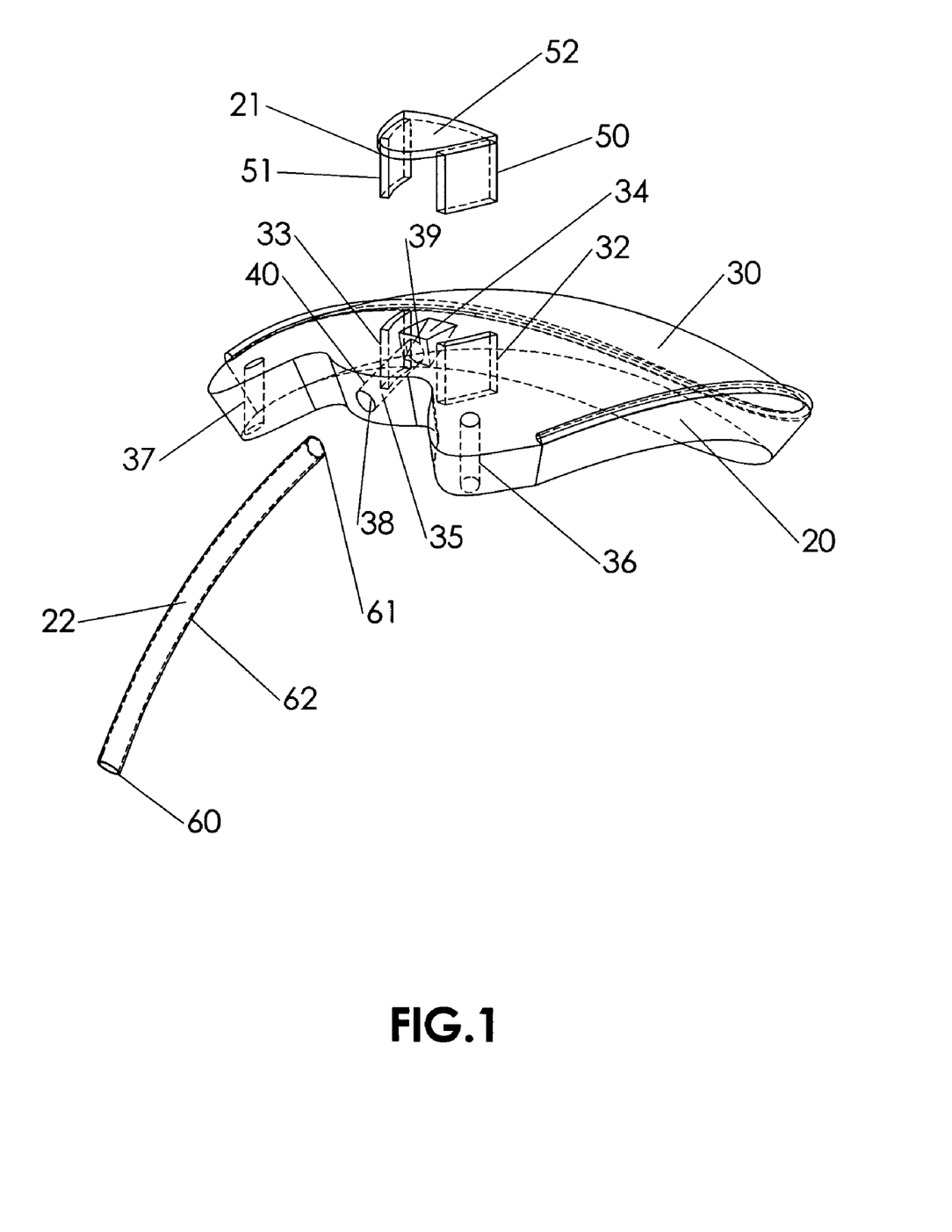
FIG. 1 is an exploded view of implant assembly
Figure 2:
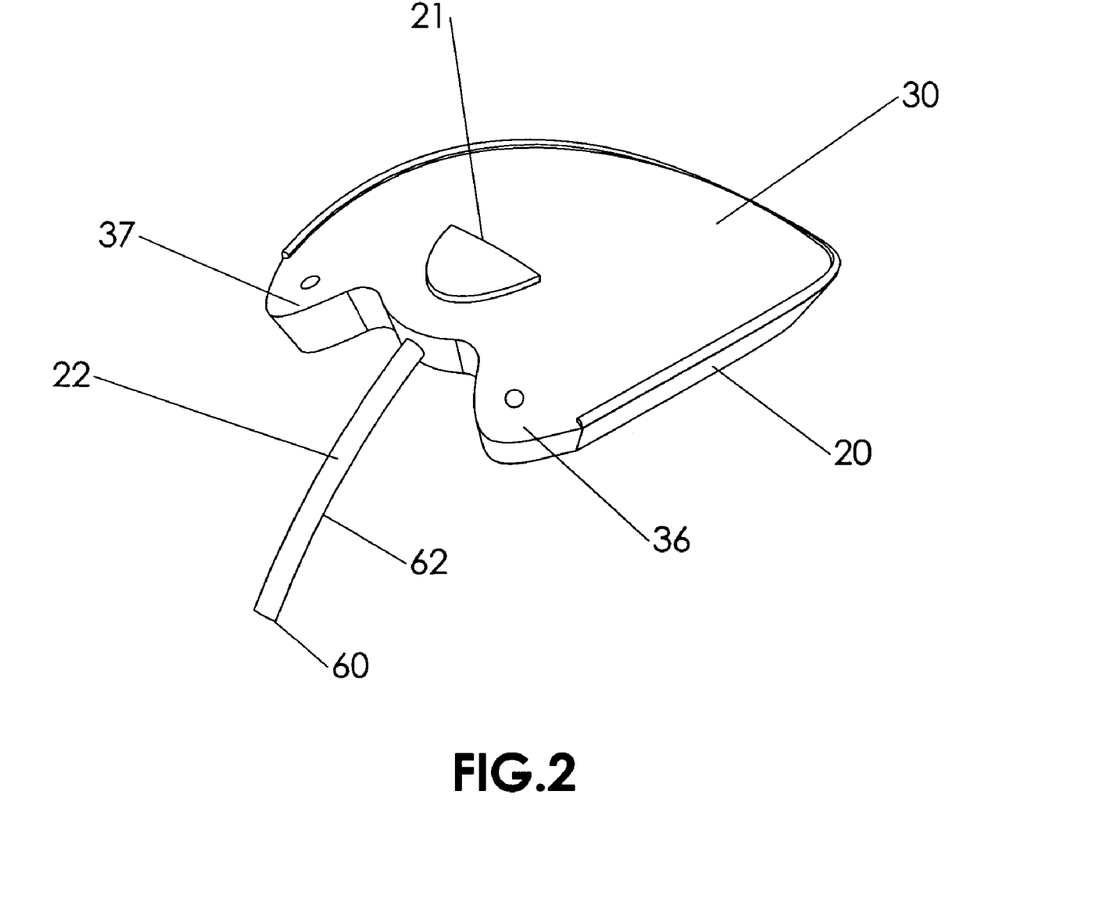
FIG. 2 is a perspective view of implant assembly
Figure 3:
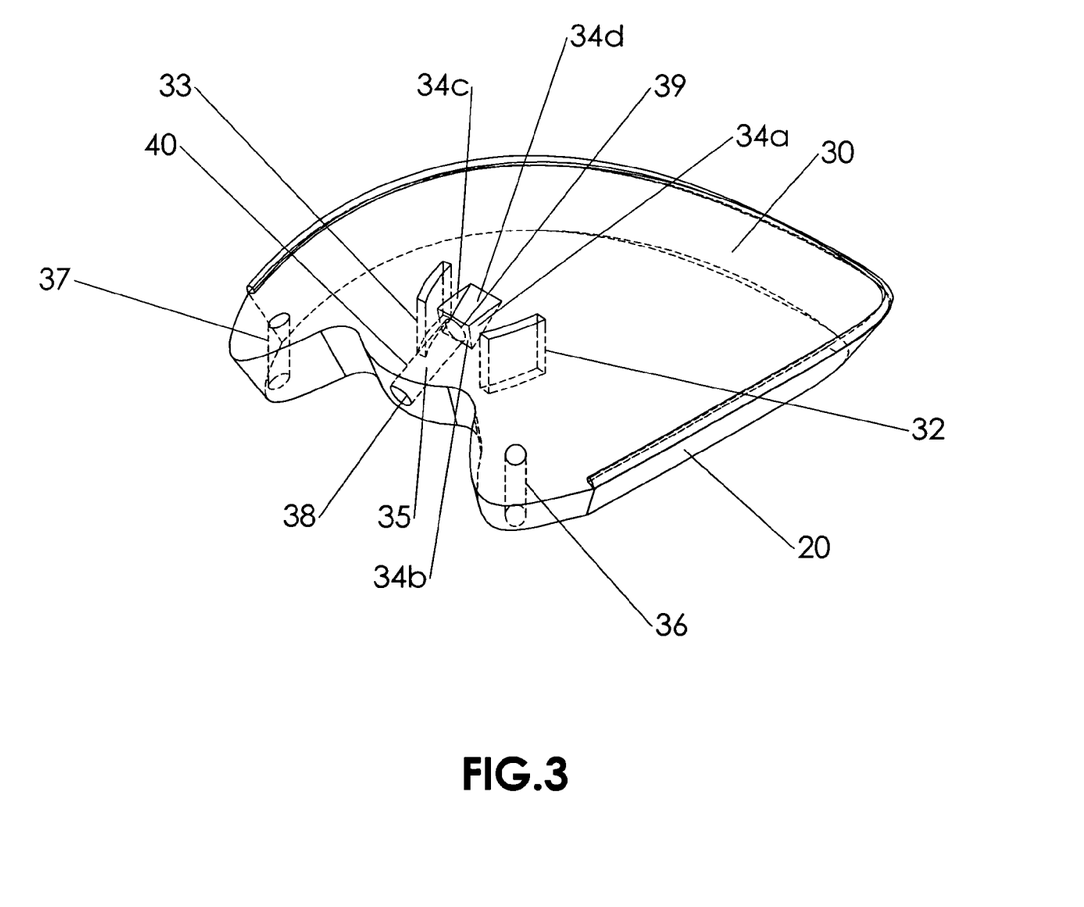
FIG. 3 is a perspective view of plate component.
Figure 4:
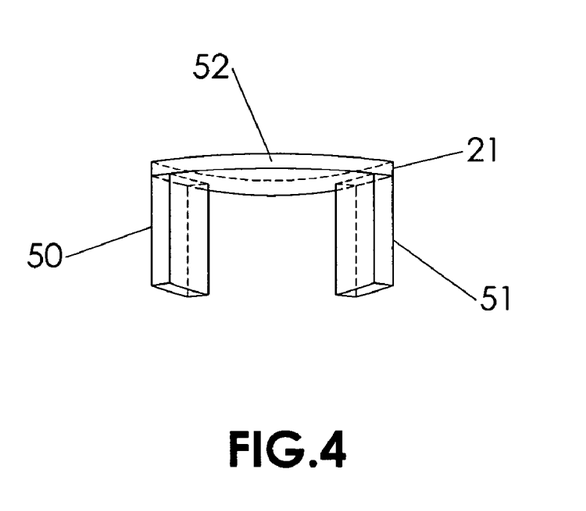
FIG. 4 is a front view of flow regulating member
Figure 5:
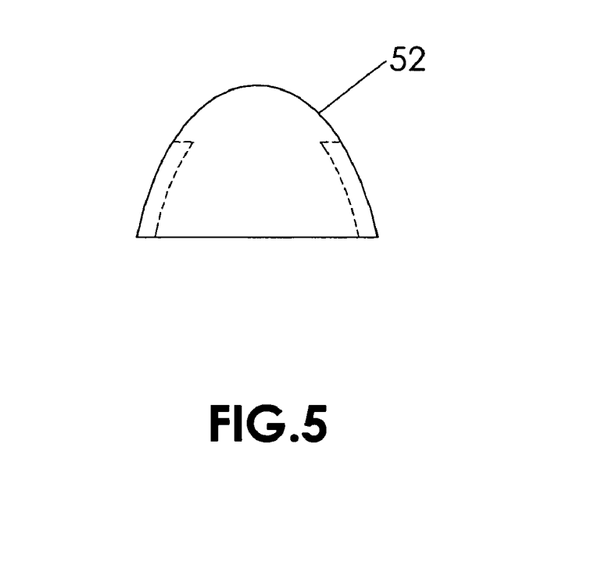
FIG. 5 is a top view of flow regulating member
Figure 6:
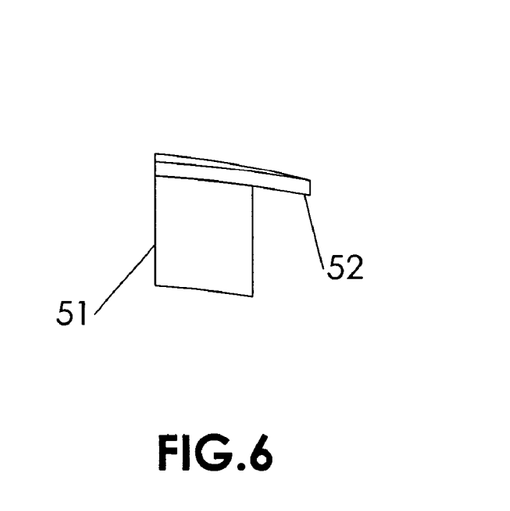
FIG. 6 is a side view of flow regulating member

As illustrated best in FIG. 1. The implant 10 of present invention is formed in parts from three components: a pliable plate 20, flow regulating member 21 and drainage tube 22. The plate 20 can be offered in different geometrical shapes (Oval, circular, Hexagonal or Trapezoidal). The plate 20 has top curved surface 30 and bottom curved surface 31 (best illustrated in FIG. 7a). The top surface 30 serves as distribution area for aqueous humor received from the anterior chamber of the eye. The curved bottom surface 31 facilitates implant seating on the globe of the eye. As shown in FIG. 3, the plate 20 includes key features that are slot 32, slot 33, pocket 34, circular passageway 35 and implant anchoring holes 36 and 37. The plate 20 is made of Silastic A manufactured by Dow Corning Corporation and is molded to desired geometric shape. The flow regulating member 21 regulates the flow of aqueous drained from the anterior chamber of the eye onto the plate surface 30. As best illustrated in FIGS. 4, 5 & 6, the flow regulating member 21 comprises of integral tab 50, tab 51 and resilient membrane 52. Preferred materials for making flow regulating member is silicone material. As shown in FIG. 1, the drainage tube 22 has proximal end 60, distal end 61 and outer surface 62. The drainage tube is made of medical grade Silicone elastomer as is offered by Nusil Corporation, CA. The implant comprising of plate 20, flow regulating member 21 and drainage tube 22, all are constructed from flexible elastomeric material, which implant provides trouble-free insertion beneath the eye and also reduces post-operative irritation, whereas all known prior arts (as discussed above) are either made of pliable material with no aqueous flow controlling mechanism or are made of hard polymeric material with less then effective valve mechanism.

As best illustrated in FIG. 1 Slot 32 and slot 33 are designed to receive tab 50 and 51 respectively. The geometrical configuration of slots 32 and 33 is same as tabs 50 and 51. As illustrated in FIG. 3, the slot 32 and slot 33 are located close to edge of face 34a and edge of face 34c respectively. The surface pocket 34 has unique geometry. The surface pocket 34 includes four faces 34a, 34b, 34c and 34d. The face 34d is blended with top surface 30 of plate 20 and ends at the bottom of the face 34 b such that the face 34d is inclined at an angle with face 34b. The circular (preferred diameter 0.025") passageway 35 embedded inside the plate thickness has proximal end 38, distal end 39 and profile surface 40. The distal end 39 terminates in face 34 b of surface pocket 34. The circular passageway 35 has curvature similar to that of top and bottom surface 30 and 31 of the plate. This prevents kinking of drainage tube 22. The implant anchoring hole 36 and hole 37 have preferred diameter 0.02"-0.025" and is used to suture implant with the tissue of the eye (Sclera).

Figures 7, 7A:
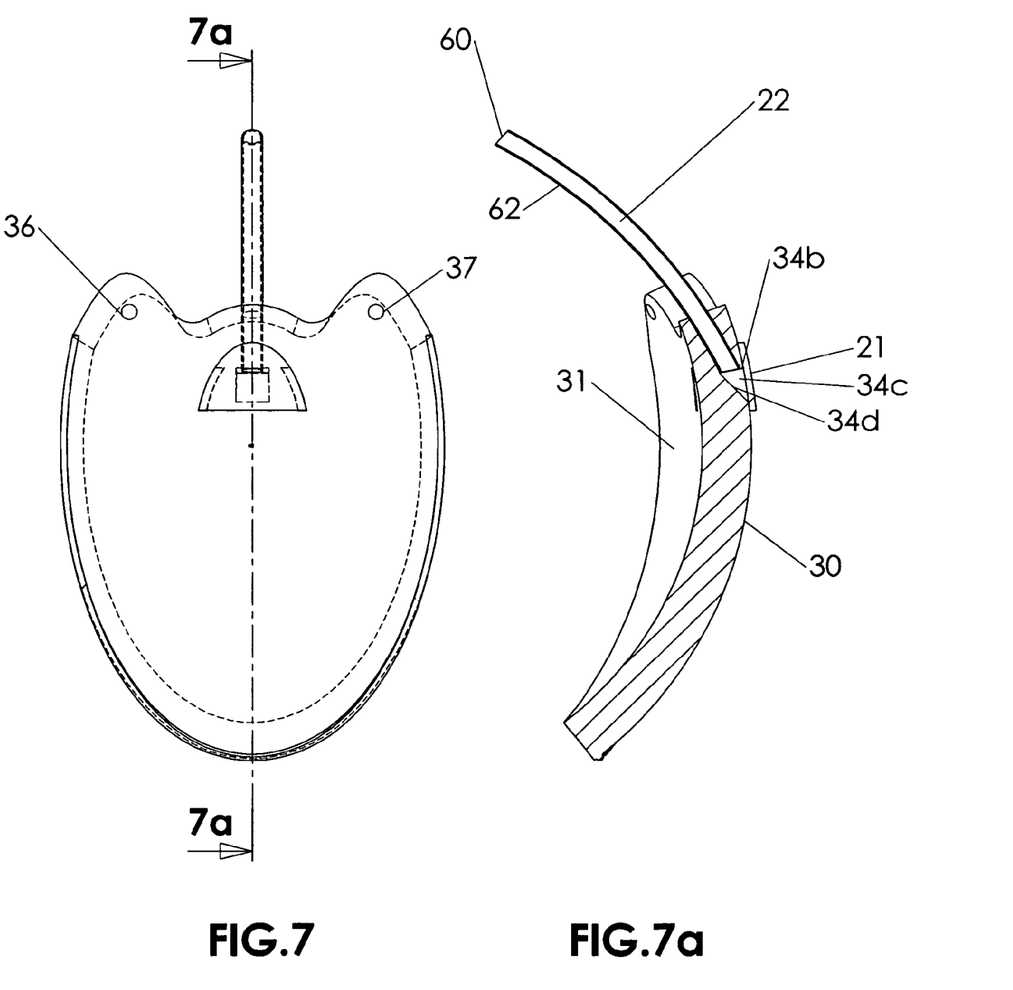
FIG. 7 is a top view of implant assembly
FIG. 7a is a cross-sectional view of implant assembly taken along 7a-7a of FIG. 7
Figure 8:
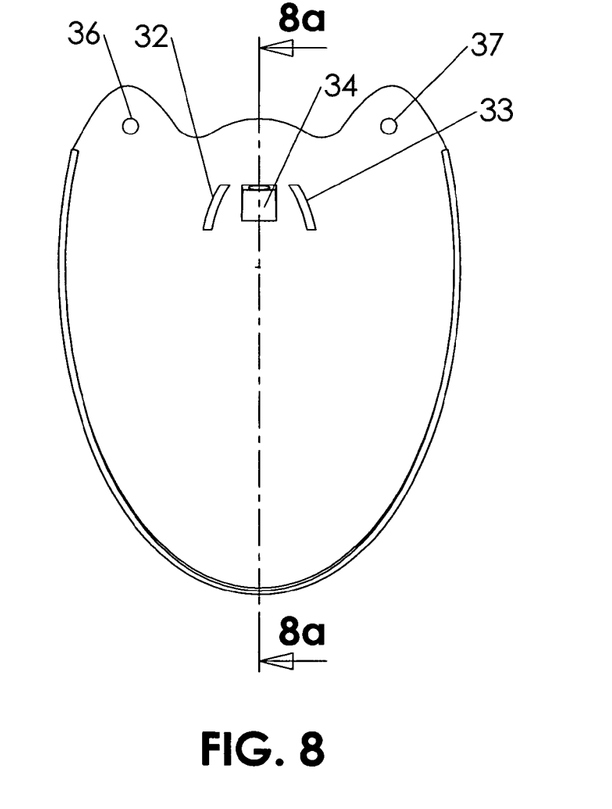
FIG. 8 is a top view of plate component
Figure 8A:
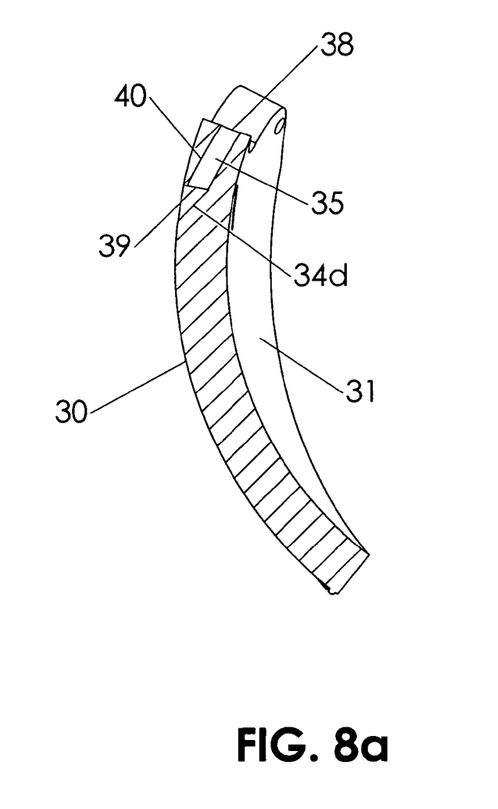
FIG. 8a is a cross-sectional view of plate component taken along 8a-8a of FIG. 8

FIG. 7 shows the Top view of the implant 10 formed in parts from plate 20, flow regulating member 21 and drainage tube 22. The flow regulating member 21 is attached to the plate 20 with tab 50 and tab 51 securely held inside slot 32 and slot 33 respectively using medical grade silicone adhesive (RTV-118 from General Electric, N.Y or silicone adhesive from Nusil corporation, CA). Once attached, the resilient membrane 52 completely covers the surface pocket 34 forming a releasable seal between the surface pocket 34 and top surface 31 of plate 20. The resilient membrane has curvature similar to that of Top surface 30 of the plate 20. The drainage tube 22 resides inside circular passageway 35 such that the distal end 61 is coincident with distal end 39 of the circular passageway 35. The outer surface 62 of the tube 22 is bonded with profile surface 40 of circular passageway 35 using medical grade silicone adhesive (RTV-118 from General Electric, N.Y or silicone adhesive from Nusil corporation, CA). The proximal end 60 of the drainage tube is inserted inside anterior chamber of the eye allowing aqueous humor to flow from the anterior chamber to the pocket 34 which is covered by resilient membrane 52, which membrane is integral part of flow regulating member 21. The resilient membrane 52 is normally biased to prevent flow through the pocket 34, but will open to permit flow through the pocket 34 when the pressure inside anterior chamber of the eye exceeds predetermined amount (generally 10 mm of Hg). A variety of pressure/flow characteristics can be provided by the present invention by providing a resilient membrane 52 in different thickness. The regulated out flowing aqueous humor gets distributed over top surface 30 of plate 20 and finally gets absorbed by the body.

Figure 9:
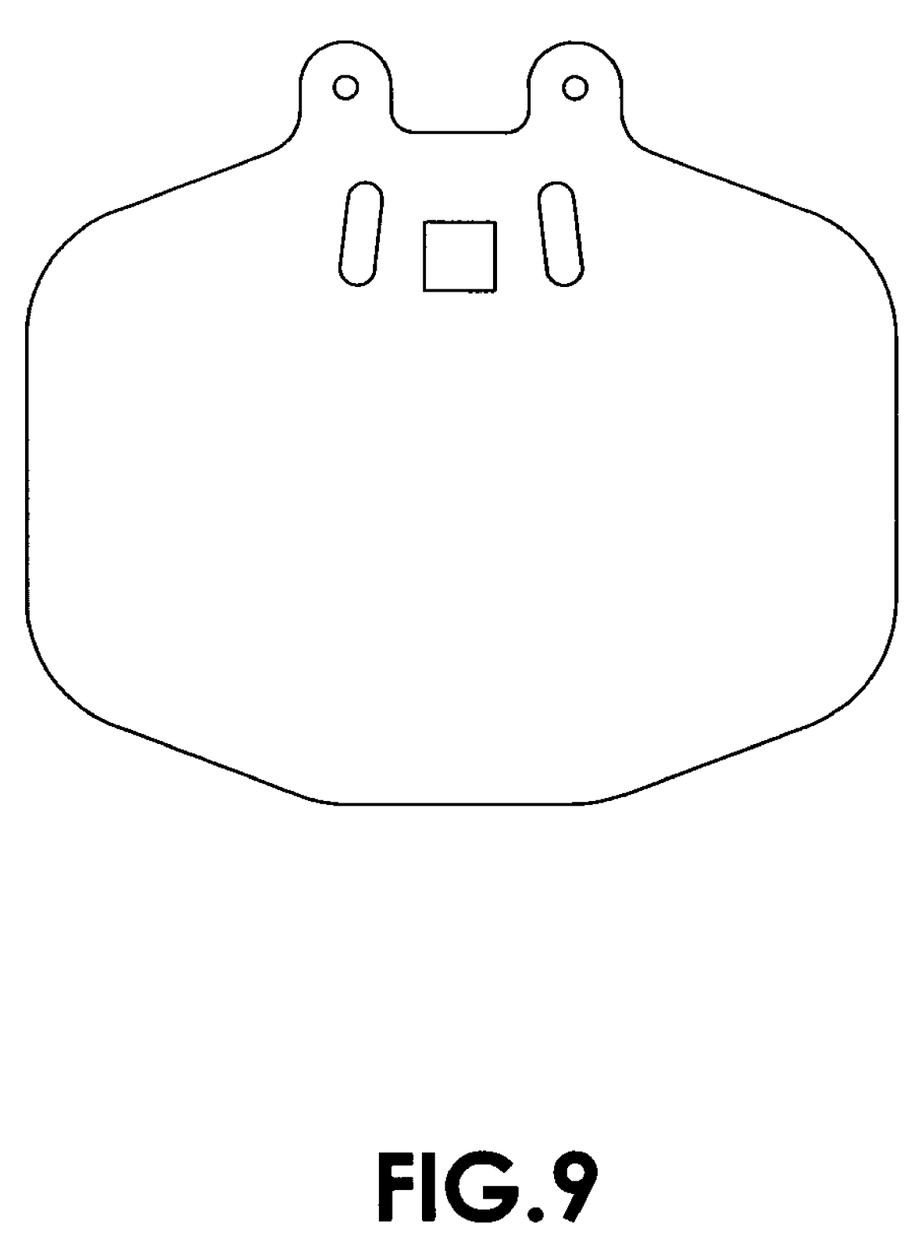
FIG. 9 is a top view of additional alternative embodiment of plate component.

FIG. 9 shows additional alternative embodiment of plate 20 illustrated in hexagonal shape. The present embodiment illustrated in FIG. 9 offers larger plate surface area which facilitates in formation of desirable bigger bleb.

I claim:

1. An aqueous humor flow regulating and drainage implant formed in parts from a molded elastomeric plate, a flow regulating member, and a drainage tube; said plate having proximal and distal regions, said proximal region of the plate containing a pocket, a circular passageway, and slots;

said circular passageway, comprising a generally curved shape, embedded inside said plate's thickness, said passageway originating from the proximal vertical edge of said plate and terminating within said pocket;

said drainage tube comprising proximal and distal ends, said tube secured inside said passageway, the outer surface of said tube coincident with and directly bonded with said passageway inside said plate, with distal end of said tube in communication with said pocket and proximal end configured to be in communication with the anterior chamber of the eye;

said flow regulating member including tabs and a resilient membrane, said tabs being securely attached to said plate inside said slots to support said membrane, said membrane being generally arch shaped and resiliently biased and configured to contact the outer surface of said plate such that said membrane completely covers said pocket, forming a releasable seal between said pocket and outer surface of said plate, said seal opening when differential pressure across the seal exceeds a threshold pressure of 10 mmHg and closing when differential pressure across the seal falls below a threshold pressure of 10 mmHg, wherein the seal remains closed at a differential pressure of 10 mmHg.

2. The implant of claim 1 wherein said pocket includes four face walls, one of said walls is blended with a top surface of said plate and ends at a bottom of an opposing face wall such that the blended face is inclined at an angle with said opposing face wall.

3. The implant of claim 2 wherein said face walls of said pocket has face edges no longer than 0.35 inches.

4. The implant of claim 1 wherein said circular passageway has a length not more than 0.6 inches.

5. The implant of claim 1 wherein the diameter of said circular passageway is not more than 0.06 inches.

6. The implant of claim 1 wherein said membrane of said flow regulating member has a curvature such that a bottom part of said membrane has a curvature similar to a top part of said plate.

7. The implant of claim 1 wherein said flow regulating member is formed of silicone.

8. The implant of claim 1 wherein said plate is formed of silicone.

9. The implant of claim 1 wherein said plate has a variable thickness.

10. The implant of claim 1 wherein said plate has a uniform thickness.

11. The implant of claim 1 wherein said pocket has a depth of no more than 0.08 inches.

* * * * *